(12) United States Patent
Heinrich et al.

(10) Patent No.: US 12,118,818 B2
(45) Date of Patent: Oct. 15, 2024

(54) APPARATUS AND METHOD FOR PERFORMING IMAGE-BASED FOOD QUANTITY ESTIMATION

(71) Applicant: KONINKLIJKE PHILIPS N.V., Eindhoven (NL)

(72) Inventors: Adrienne Heinrich, Eindhoven (NL); Lu Wang, Eindhoven (NL); Zhaorui Yuan, Eindhoven (NL); Marija Despenic, Eindhoven (NL)

(73) Assignee: VERSUNI HOLDING B.V., Eindhoven (NL)

( * ) Notice: Subject to any disclaimer, the term of this patent is extended or adjusted under 35 U.S.C. 154(b) by 267 days.

(21) Appl. No.: 17/625,277

(22) PCT Filed: Jul. 8, 2020

(86) PCT No.: PCT/EP2020/069211
§ 371 (c)(1),
(2) Date: Jan. 6, 2022

(87) PCT Pub. No.: WO2021/005095
PCT Pub. Date: Jan. 14, 2021

(65) Prior Publication Data
US 2022/0254175 A1    Aug. 11, 2022

(30) Foreign Application Priority Data

Jul. 11, 2019 (EP) .................... 19185688

(51) Int. Cl.
*G06V 40/10* (2022.01)
*G06V 40/60* (2022.01)
(Continued)

(52) U.S. Cl.
CPC .......... *G06V 40/107* (2022.01); *G06V 40/117* (2022.01); *G06V 40/67* (2022.01);
(Continued)

(58) Field of Classification Search
CPC .... G06V 40/107; G06V 40/117; G06V 40/67; G06V 20/68; G16H 20/60; G16H 30/40
See application file for complete search history.

(56) References Cited

U.S. PATENT DOCUMENTS 5,454,721 A * 10/1995 Kuch ................. G09B 19/0092
434/428
8,345,930 B2    1/2013 Tamrakar et al.
(Continued)

FOREIGN PATENT DOCUMENTS

CN            104778374 A        7/2015

OTHER PUBLICATIONS

Piernas, C., et al., "Trends In Snacking Among U.S. Children", Health Affairs, vol. 29, Issue 3, pp. 398-404, Mar. 2010.
(Continued)

*Primary Examiner* — Xuemei G Chen
(74) *Attorney, Agent, or Firm* — Maschoff Brennan (57) ABSTRACT

A computer-implemented method for performing image-based food quantity estimation is provided. The method includes acquiring a first image, when the first image depicts a food item and a body part of a first user. The method further includes detecting, based on the acquired first image, a first physical attribute of the body part of the first user. The method furthermore includes identifying, based on the acquired first image, the depicted food item, and estimating a quantity of the food item depicted in the acquired first image based on the identified food item and the detected first physical attribute of the body part of the user.

14 Claims, 4 Drawing Sheets

(51) Int. Cl.
*G16H 20/60* (2018.01)
*G16H 30/40* (2018.01)
*G06V 20/68* (2022.01)

(52) U.S. Cl.
CPC .............. *G16H 20/60* (2018.01); *G16H 30/40* (2018.01); *G06V 20/68* (2022.01)

(56) References Cited

U.S. PATENT DOCUMENTS

| | | | |
|---|---|---|---|
| 9,741,172 B2 | 8/2017 | Breedvelt-Schouten et al. | |
| 10,149,958 B1* | 12/2018 | Tran ........................ | G16H 50/20 |
| 10,790,054 B1* | 9/2020 | Vleugels ................ | G16H 20/60 |
| 2002/0027164 A1* | 3/2002 | Mault ..................... | G16H 20/30 |
| | | | 235/462.46 |
| 2003/0076983 A1* | 4/2003 | Cox ......................... | G06F 18/00 |
| | | | 382/110 |
| 2008/0267444 A1* | 10/2008 | Simons-Nikolova ..... | G06T 7/20 |
| | | | 382/100 |
| 2010/0111383 A1* | 5/2010 | Boushey .................. | G06F 18/00 |
| | | | 382/128 |
| 2013/0335418 A1* | 12/2013 | Kim ........................ | G16H 20/60 |
| | | | 345/424 |
| 2013/0336519 A1 | 12/2013 | Connor | |
| 2015/0151050 A1* | 6/2015 | Estes ..................... | A61M 5/172 |
| | | | 604/151 |
| 2015/0168365 A1* | 6/2015 | Connor .................. | A61B 5/681 |
| | | | 356/402 |
| 2015/0228062 A1* | 8/2015 | Joshi ...................... | G06Q 50/12 |
| | | | 382/110 |
| 2015/0324698 A1* | 11/2015 | Karaoguz ............... | H04L 67/12 |
| | | | 706/46 |
| 2015/0332620 A1* | 11/2015 | Sako ...................... | G06T 19/006 |
| | | | 345/8 |
| 2016/0012749 A1 | 1/2016 | Connor | |
| 2016/0034764 A1* | 2/2016 | Connor .................. | G06V 20/52 |
| | | | 348/158 |
| 2016/0203365 A1* | 7/2016 | Breedvelt-Schouten .................... | G02B 27/017 |
| | | | 345/633 |
| 2016/0292390 A1 | 10/2016 | Sculati | |
| 2017/0323481 A1* | 11/2017 | Tran ...................... | H04N 23/611 |
| 2018/0235538 A1* | 8/2018 | Connor .................. | G16H 20/60 |
| 2019/0333634 A1* | 10/2019 | Vleugels .............. | A61B 5/1121 |
| 2020/0005455 A1* | 1/2020 | Alshurafa .............. | G01N 21/27 |
| 2020/0342977 A1* | 10/2020 | Son ........................ | G06Q 50/12 |

OTHER PUBLICATIONS

Almaghrabi, R., et al., "A Novel Method for Measuring Nutrition Intake Based on Food Image", IEEE International Instrumentation and Measurement Technology Conference (I2MTC), IEEE, pp. 366-370, May 13, 2012.

Fujishima, N., et al., "Fingernail Detection in Hand Images using Difference of Nail-color Pixels' Density between Vicinity Areas of Fingernails and Skin", The 1st IEEE Global Conference on Consumer Electronics, pp. 233-237, 2012.

Sharma, V., et al., "Nail Color and Texture Analysis for Disease Detection", International Journal of Bio-Science and Bio-Technology, vol. 7, Issue 5, pp. 351-358, 2015.

Wu, H., et al., "Learning to Make Better Mistakes: Semantics-Aware Visual Food Recognition", Proceedings of the 24th ACM international conference on Multimedia, pp. 172-176, Oct. 2016.

Barros Barbosa, I., et al., "On the Use of Fingernail Images as Transient Biometric Identifiers", Machine Vision and Applications, vol. 27, Issue 1, pp. 65-76, 2016.

Puggal, S., et al., "Enhanced Fingernail Recognition Based on GLCM, SIFT and NN", International Journal of Computer Applications, vol. 180, Issue 26, pp. 18-22, Mar. 2018.

Extended European Search Report issued in connection with corresponding EP Application No. 19185688.9 dated Jan. 20, 2020.

International Search Report and Written Opinion issued in connection with corresponding PCT Application No. PCT/EP2020/069211 dated Oct. 14, 2020.

\* cited by examiner

APPARATUS AND METHOD FOR PERFORMING IMAGE-BASED FOOD QUANTITY ESTIMATION

CROSS-REFERENCE TO RELATED APPLICATIONS

The present application is a U.S. National Phase application under 35 U.S.C. § 371 of International Application No. PCT/EP2020/069211, filed on Jun. 8, 2020, which claims the benefit of European Patent Application No. 19185688.9, filed on Jul. 11, 2019. These applications are hereby incorporated by reference herein.

FIELD OF THE INVENTION

The present disclosure relates to an apparatus and method for performing image-based food quantity estimation.

BACKGROUND OF THE INVENTION

Studies have shown that a healthy diet can significantly reduce the risk of diseases. However, typically individuals, especially children, are not apt at assessing their own dietary intake accurately. The assessment of caloric and nutrient content is especially difficult when eating at a restaurant as most restaurants do not provide menus that list the dietary energy values associated with their dishes. Accordingly, there is a demand for a systematic technique for monitoring and assessing dietary intake (e.g. dietary energy or other types of nutrients) by way of allowing users to estimate quantities of the food being consumed.

SUMMARY OF THE INVENTION

A number of techniques have been proposed in the field of image-based food quantity estimation. For example, one proposed technique involves the use of a three-dimensional (3D) marker with patterns to help estimate the focal length of food images, which requires the use of a specific reference object which may make it difficult for children to use the technique correctly. Another proposed technique uses a thumb as the reference to estimate the volume of food in a container. This technique operates on the basis that the dimensions of the thumb is known, and that the entire width of the thumbnail is visible and detectable in the images. With this technique, there is no personalization or flexibility in terms of features or characteristics around the thumbnail for computing the dimensions of the thumb. Therefore, the robustness of dimension computation is compromised especially when used in varying lighting and background conditions.

Yet another proposed technique quantifies food items depicted in images on the basis of a body part of a user, e.g. the hand of the user. This technique estimates the anthropometric parameter(s) such as the width of the hand, the palm area of the hand, the length of the index finger, and the width of the finger (index, middle, or annular), and requires post-processing of the extracted features via user interactions for the purpose of calibration as well as a specific reference point (e.g. a hand support) for determining the absolute values of the estimated/measured distances. The quantities of the food items can then be estimated based on the absolute values of the anthropometric parameter(s). This approach heavily relies on the extraction of color features from images, and furthermore the specific reference point is required to have a different color from any possible skin colors. Moreover, this approach also requires the images to be acquired at a particular angle and distance with respect to the body part and/or the specific reference point and that the body part to be completely visible in the images. These all pose an impact on the usability and convenience of estimating food quantity.

As noted above, there are a number of disadvantages associated with the currently available solutions for performing image-based food quantity estimation, for example requiring specific reference objects, requiring complete visibility of reference objects and/or body parts, and also the lack in flexibility for personalization, all of which compromising the robustness or the usability of the estimation technique. It would therefore be advantageous to provide an improved method for performing image-based food quantity estimation which can overcome the disadvantages mentioned above.

To better address one or more of the concerns mentioned earlier, in a first aspect, a computer-implemented method for performing image-based food quantity estimation is provided. The method comprises: acquiring a first image, wherein the first image depicts a food item and a body part of a first user; detecting, based on the acquired first image, a first physical attribute of the body part of the first user; identifying, based on the acquired first image, the depicted food item; and estimating a quantity of the food item depicted in the acquired first image based on the identified food item and the detected first physical attribute of the body part of the user.

In some embodiments, the method may further comprise: acquiring, for each of a plurality of users, one or more physical attributes of the body part of the respective user; associating, for each of the plurality of users, the acquired one or more physical attributes of the body part with a user profile of the respective user in a user profile database; identifying the first user by comparing the detected first physical attribute of the body part of the first user with the corresponding type of physical attribute of the body part of the plurality of users stored in the user profile database; and retrieving a second physical attribute of the body part of the first user from the user profile of the first user. In these embodiments, estimating the quantity of the food item may be further based on the retrieved second physical attribute of the body part of the first user.

In some embodiments, acquiring one of more physical attributes of the body part of the respective user may comprise: providing, at a touch screen display device, a virtual user interface including an interactive visual tool configured to allow the user to measure the one or more physical attributes of the body part of the respective user; receiving a user input via the virtual user interface. In these embodiments, the user input corresponds to a placement of at least a part of the body part at the touch screen display device; and determining the one or more physical attributes of the body part based on the received user input.

In some embodiments, acquiring one or more physical attributes of the body part of the respective user comprises: acquiring a second image depicting the body part of the respective user; detecting, from the acquired second image, a first image descriptor feature associated with the body part of the respective user; and determining the one or more physical attributes based on the detected first image descriptor feature.

In some embodiments, the method may further comprise: acquiring one or more manually-measured physical attributes of the body part of the respective user; comparing each of the one or more determined physical attributes respectively with the corresponding one or more manually-measured physical attributes; and confirming or updating the value of the one or more physical attributes of the body part based on results of the comparison.

In some embodiments, the method may further comprise performing the following steps for at least one of the plurality of users: acquiring one or more third images depicting the body part of the respective user; performing image processing of the acquired one or more third images depicting the body part of the respective user to obtain a second image descriptor feature associated with the body part of the respective user, wherein the image processing is performed based on comparison between image pixels of the one or more third images; determining, based on the second image descriptor feature of the one or more third images, the one or more physical attributes of the body part of the respective user which correspond to the acquired one or more physical attributes of the body part of the respective user; calibrating the acquired one or more physical attributes of the body part of the respective user based on comparison between the acquired one or more physical attributes and the one or more physical attributes determined based on the second image descriptor feature; and updating, based on results of the calibration, the one or more physical attributes of the body part associated with the user profile of the respective user.

In some embodiments, a plurality of third images depicting the body part of the respective user may be acquired, and a plurality of types of image descriptor features may be obtained for each of the plurality of third images. In these embodiments, acquiring one or more physical attributes of the body part of the respective user may further comprise: determining a degree of certainty of a type of image descriptor features by comparing types of image descriptor features of each of the plurality of third images; and selecting the type of image descriptor feature with a highest degree of certainty. Furthermore, in these embodiments, determining the one or more physical attributes of the body part of the respective user may be based on one or more image descriptor features which correspond to the selected type of image descriptor feature with the highest degree of certainty.

In some embodiments, acquiring the one or more physical attributes of the body part of the respective user may comprise: acquiring one or more physical characteristics of the respective user. In these embodiments, the one or more physical characteristics may comprise at least one of: the gender of the respective user, the age of the respective user, the height of the respective user, and the weight of the respective user; and determining the one or more physical attributes of the body part of the respective user based on the one or more physical characteristics of the respective user.

In some embodiments, the method may further comprise performing image processing on the first image to extract image pixels corresponding to the depicted food item. In these embodiments, estimating the quantity of the food item may be based on comparison between the extracted image pixels corresponding to the depicted food item.

In some embodiments, the method may further comprise acquiring a camera angle at which the first image is taken. In these embodiments, estimating the quantity of the depicted food item is further based on the acquired camera angle.

In some embodiments, the method may further comprise: acquiring a supplementary image depicting the body part of the first user, wherein the supplementary image is taken at a different camera angle from that of the first image; performing, based on the supplementary image, detection of the first physical attribute of the body part of the first user; and updating the value of the first physical attribute of the body part of the first user based on comparison between the result of the detection based on the first image and the result of the detection based on the supplementary image.

In some embodiments, the method may further comprise determining a characteristic associated with the quantity of the food item depicted in the first image, based on the estimated quantity of the food item.

In some embodiments, the characteristic associated with the quantity of the food item may be one of: an amount of dietary energy in the food item, an amount of protein in the food item, an amount of carbohydrate in the food item, an amount of mineral in the food item, an amount of vitamins in the food item, an amount of dietary fiber in the food item, and an amount of sugar in the food item.

In a second aspect, there is provided a computer program comprising a computer readable medium, the computer readable medium having computer readable code embodied therein, the computer readable code being configured such that, on execution by a suitable computer or processor, the computer or processor is caused to perform the method as described herein.

In a third aspect, there is provided an apparatus for performing image-based food quantity estimation, the apparatus comprising a processor configured to: acquire a first image, wherein the first image depicts a food item and a body part of a first user; detect, based on the acquired first image, a first physical attribute of the body part of the first user; identify, based on the acquired first image, the depicted food item; and estimate a quantity of the food item depicted in the acquired first image based on the identified food item and the detected first physical attribute of the body part of the user.

According to the aspects and embodiments described above, the limitations of existing techniques are addressed. In particular, the above-described aspects and embodiments enable image-based food quantity estimation to be performed in a user-friendly and accurate manner. There is thus provided an improved method and apparatus for performing image-based food quantity estimation. These and other aspects of the disclosure will be apparent from and elucidated with reference to the embodiment(s) described hereinafter.

BRIEF DESCRIPTION OF THE DRAWINGS

For a better understanding of the embodiments, and to show more clearly how they may be carried into effect, reference will now be made, by way of example only, to the accompanying drawings, in which.

DETAILED DESCRIPTION OF EMBODIMENTS

As noted above, there is provided an improved apparatus and a method of operating the same which addresses the existing problems.

Figure 1:
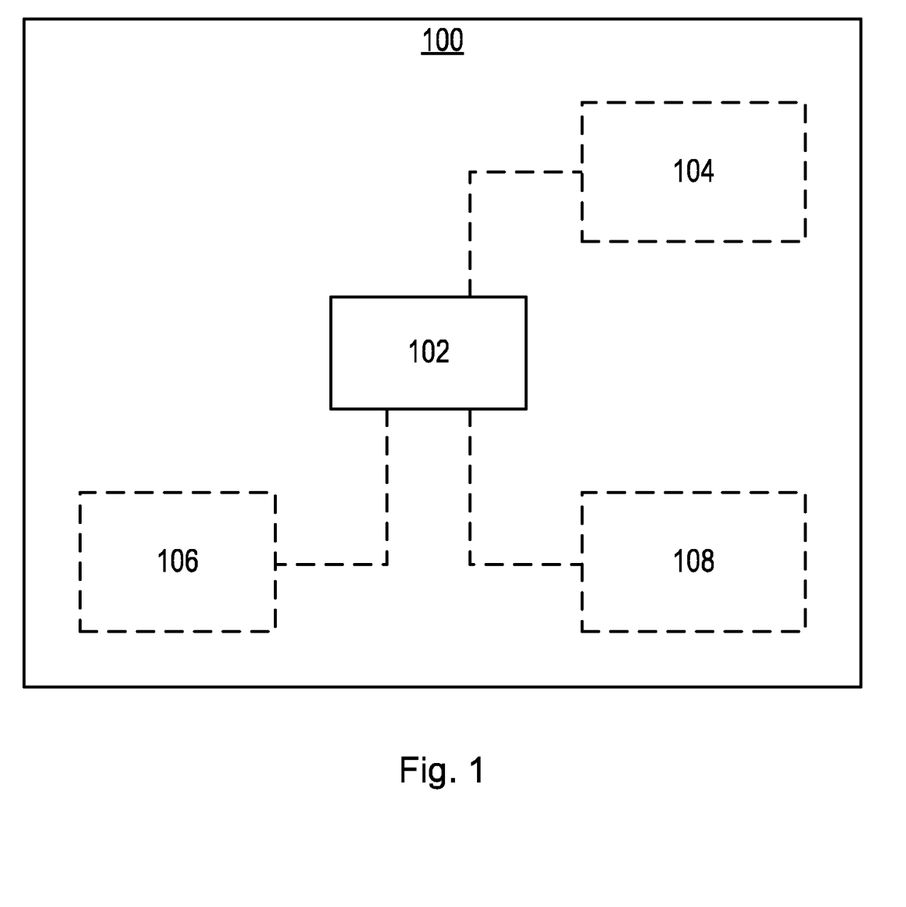
FIG. 1 is a block diagram of an apparatus for performing image-based food quantity estimation, according to an embodiment.

FIG. 1 shows a block diagram of an apparatus 100 according to an embodiment, which can be used for performing image-based food quantity estimation. Although the some of the operation of the apparatus 100 is described below in the context of a single user, it will be appreciated that the apparatus 100 is capable of performing image-based food quantity estimation based on images depicting the body parts of multiple users.

As illustrated in FIG. 1, the apparatus comprises a processor 102 that controls the operation of the apparatus 100 and that can implement the method described herein. The processor 102 can comprise one or more processors, processing units, multi-core processor or modules that are configured or programmed to control the apparatus 100 in the manner described herein. In particular implementations, the processor 102 can comprise a plurality of software and/or hardware modules that are each configured to perform, or are for performing, individual or multiple steps of the method described herein.

Briefly, the processor 102 is configured to acquire a first image that depicts a food item and a body part of a first user, and to detect, based on the acquired first image, a first physical attribute. The processor 102 is further configured to identify the depicted food item based on the acquired first image and to estimate a quantity of the food item based on the identified food item and the detected first physical attribute of the body part of the user.

In some embodiments, the apparatus 100 may further comprise at least one user interface 104. Alternative or in addition, at least one user interface 104 may be external to (i.e. separate to or remote from) the apparatus 100. For example, at least one user interface 104 may be part of another device. A user interface 104 may be for use in providing a user of the apparatus 100 with information resulting from the method described herein. Alternatively or in addition, a user interface 104 may be configured to receive a user input. For example, a user interface 104 may allow a user of the apparatus 100 to manually enter instructions, data, or information. In these embodiments, the processor 102 may be configured to acquire the user input from one or more user interfaces 104.

A user interface 104 may be any user interface that enables the rendering (or output or display) of information to a user of the apparatus 100. Alternatively or in addition, a user interface 104 may be any user interface that enables a user of the apparatus 100 to provide a user input, interact with and/or control the apparatus 100. For example, the user interface 104 may comprise one or more switches, one or more buttons, a keypad, a keyboard, a touch screen or an application (for example, on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces.

In some embodiments, the apparatus 100 may comprise a memory 106. Alternatively or in addition, one or more memories 106 may be external to (i.e. separate to or remote from) the apparatus 100. For example, one or more memories 106 may be part of another device. A memory 106 can be configured to store program code that can be executed by the processor 102 to perform the method described herein. A memory can be used to store information, data, signals and measurements acquired or made by the processor 102 of the apparatus 100. For example, a memory 106 may be used to store (for example, in a local file) the first physical attribute of the first user. The processor 102 may be configured to control a memory 106 to store the first physical attributes of the first user.

In some embodiments, the apparatus 100 may comprise a communications interface (or circuitry) 108 for enabling the apparatus 100 to communicate with any interfaces, memories and/or devices that are internal or external to the apparatus 100. The communications interface 108 may communicate with any interfaces, memories and/or devices wirelessly or via a wired connection. For example, the communications interface 108 may communicate with one or more user interfaces 104 wirelessly or via a wired connection. Similarly, the communications interface 108 may communicate with the one or more memories 106 wirelessly or via a wired connection.

It will be appreciated that FIG. 1 only shows the components required to illustrate an aspect of the apparatus 100 and, in a practical implementation, the apparatus 100 may comprise alternative or additional components to those shown.

Figure 2:
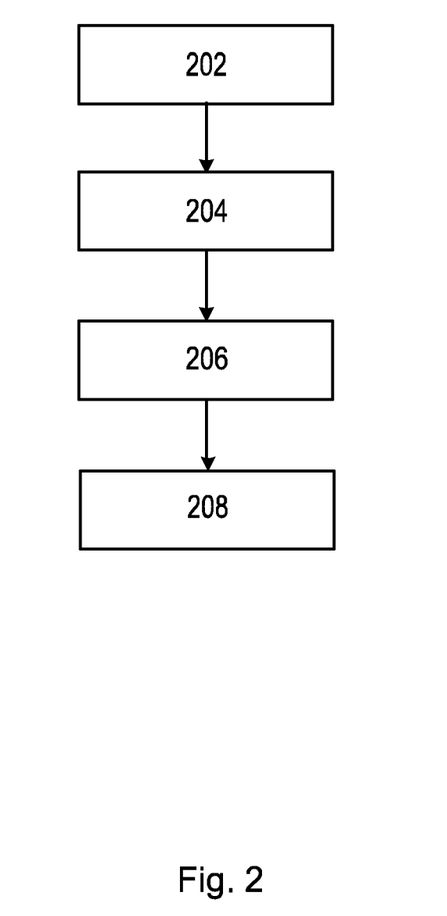
FIG. 2 illustrates a computer-implemented method for performing image-based food quantity estimation, according to an embodiment.

FIG. 2 illustrates a computer-implemented method for performing image-based food quantity estimation, according to an embodiment. The illustrated method can generally be performed by or under the control of processor 102 of the apparatus 100.

With reference to FIG. 2, at block 202, a first image is acquired. Specifically, in some embodiments the first image may be acquired by the processor 102, for example from a smartphone camera. The first image depicts a food item and a body part of a first user. A first physical attribute of the body part of the first user is detected at block 204, the detection being based on the first image acquired at block 202.

In some embodiments, the first physical attribute may correspond to a distance between two individual points at the body part of the first user, or an area defined by three or more individual points at the body part of the first user. For example, in some embodiments the body part may be a finger of the first user. In this case, the first physical attribute may be the length of the finger of the first user (i.e. the distance between the tip of the finger and the base of the finger). As another example, in some embodiments the first physical attribute may be the width of the finger at a position of the distal knuckle of the finger. Further examples of the first physical attribute will be described in more detail with reference to FIG. 3.

Returning to FIG. 2, at block 206, the depicted food is identified based on the first image acquired at block 202, and at block 208, a quantity of the food item in the first image acquired at block 202 is estimated based on the food item identified at block 206 and the first physical attribute of the body part of the user detected at block 204. In some embodiments, the identification of the depicted food item at block 206 may be performed using currently available food visual recognition techniques, such as one proposed in "Learning to Make Better Mistakes: Semantics-Aware Visual Food Recognition" (W, Hui, Michele Merler, Roserio Uceda-Sosa, and John R. Smith; In Processing of the 2016 ACM on Multimedia Conference-MM'16, 172-76; Amsterdam, The Netherlands: ACM Press).

The method described herein may be applicable to a plurality of users. In particular, in some embodiments, the method may further comprise acquiring, for each of a plurality of users, one or more physical attributes of the body part of the respective user, and associating, for each of the plurality of users, the acquired one or more physical attributes of the body part with a user profile of the respective user in a user profile database. In these embodiments, the plurality of users may include the first user as referenced above. Moreover, in these embodiments, each of the one or more physical attributes may correspond to a distance between two individual points at the body part of the respective user (e.g. the length of a finger of the respective user).

In some embodiments, the acquiring of the one or more physical attributes of the body part of the respective user may comprise providing a virtual user interface at a touch screen display device, the virtual user interface including an interactive visual tool configured to allow the respective user to measure the one or more physical attributes of the body part of the respective user, receiving a user input via the virtual user interface, and determining the one or more physical attributes of the body part based on the received user input. In these embodiments, the user input may correspond to a placement of at least a part of the body part of the respective user at the touch screen display device. For example, the interactive visual tool may provide instructions for the respective user to press the body part (e.g. a thumb) against the touch screen display device, and the contact area detected at the touch screen display device can then be used to determine one or more physical attributes of the respective user, given the dimensions of the touch screen display device are known. Moreover, in these embodiments, the touch screen display device may be implemented as part of the user interface 104 of the apparatus 100.

In addition or alternatively, the acquiring of the one or more physical attributes of the body part of the respective user may comprise acquiring a second image depicting the body part of the user, detecting a first image descriptor feature associated with the body part of the respective user, and determining the one or more physical attributes based on the detected first image descriptor feature. The first image descriptor feature may comprise at least one of: a scale invariant feature transform (SIFT) feature of the body part extracted from the second image, a color feature of the body part extracted from the second image, a texture feature of the body part extracted from the second image, a histogram of oriented gradients of the second image, and convolution kernels of the second image. The convolution kernels may be the result of convolving the second image with different kernels. In this case, the convolving operation may be performed by the processor 102 of the apparatus 100. The first image descriptor feature may also be representative of a physical feature of the body part of the respective user, for example an edge of the body part, a specific point on the body part, a scar on the body part, a wrinkle line on the body part, a tattoo on the body part, or a mole on the body part. In some embodiments, the first image descriptor feature may be indicative of a skin type of the body part of the respective user.

In addition, the method may further comprise acquiring one or more manually-measured physical attributes of the body part of the respective user, comparing each of the one or more determined physical attributes respective with the corresponding one or more manually-measured physical attributes, and confirming or updating the value of the one or more physical attributes of the body part based on result of the comparison.

Furthermore, in some embodiments the method may further comprise identifying the first user (who may be one of the plurality of users). This identification may be performed by comparing the first physical attribute detected at block 204 with the corresponding type of physical attribute of the body part of the plurality of users stored in the user profile database. A type of physical attribute of the body part may correspond to a distance between two specific individual points at the body part of the first user or may correspond to an area defined by three or more individual points at the body part of the first user. For example, "length of thumb" may be a type of physical attribute and "width of thumb at the distal knuckle" may be a different type of physical attribute. Subsequent to identifying the first user, the method may further comprise retrieving a second physical attribute of the body part of the first user from the user profile of the first user. The second physical attribute may be of a different type from the first physical attribute but in some embodiments the first and second physical attributes may be of the same type, e.g. a wrinkle line on the body part. In these embodiments, estimating the quantity of the food item at block 208 may be further based on the retrieved second physical attribute of the body part of the first user.

In embodiments where the method comprises acquiring, for each of a plurality of users, one or more physical attributes of the body part of the respective user, the method may also further comprise acquiring, for at least one of the plurality of users, one or more third images depicting the body part of the respective user. In these embodiments, the method may comprise performing image processing of the acquired one or more third images to obtain a second image descriptor feature associated with the body part of the respective user (i.e. the at least one of the plurality of users), determining, based on the second image descriptor, of the one or more third images, the one or more physical attributes of the body part of the respective user which correspond to the acquired one or more physical attributes of the body part of the respective user, calibrating the acquired one or more physical attributes of the body part of the respective user based on comparison between the acquired one or more physical attributes and the one or more physical attributes determined based on the second image descriptor feature, and updating, based on results of the calibration, the one or more physical attributes of the body part associated with the user profile of the respective user.

In these embodiments, the image processing of the acquired one or more third images may be performed based on comparison between image pixels of the one or more third images. The second image descriptor feature may comprise at least one of: a scale invariant feature transform (SIFT) feature of the body part extracted from the respective third image, a color feature of the body part, a texture feature of the body part, a histogram of oriented gradients of the respective third image, and a convolution kernels of the third image. In this case, the convolving operation may be performed by the processor 102 of the apparatus 100. The second image descriptor feature may also be representative of a physical feature of the body part of the respective user, for example an edge of the body part, a specific point on the body part, a scar on the body part, a wrinkle line on the body part, a tattoo on the body part, or a mole on the body part. In some embodiments, the second image descriptor feature may be indicative of a skin type of the body part of the respective user.

Furthermore, in embodiments where a plurality of third images depicting the body part of the respective user are acquired, and a plurality of types of image descriptor features are obtained for each of the plurality of third images, the acquiring of one or more of physical attributes of the body part of the respective user may further comprise: determining a degree of certainty of a type of image descriptor features of each of the plurality of third images, and selecting the type of image descriptor feature with a highest degree of certainty. Certainty may be determined based on at least one of a deep learning training model and a support vector machine (SVM) training model. In these embodiments, determining the one or more physical attributes of the body part of the respective user may be based on one or more image descriptor features which correspond to the selected type of image descriptor feature with the highest degree of certainty.

In some embodiments, acquiring the one or more attributes of the body part of the respective user may comprise acquiring one or more physical characteristics of the respective user and determining the one or more physical attributes of the body part of the respective user based on the one or more physical characteristics of the respective user. In these embodiments, the one or more physical characteristics may comprise at least one of: the gender of the respective user, the age of the respective user, the height of the respective user, and the weight of the respective user. The determination of the one or more physical attributes may be based on comparing the one or more physical characteristics of the respective user against data contained in an existing population module which correlates physical attributes with physical characteristics (e.g. average thumb length for a 5 year old female child).

In some embodiments, the method may further comprise performing image processing on the first image to extract image pixels corresponding to the depicted food item. In these embodiments, estimating the quantity of the food item in block 208 may be based on comparison between the extracted image pixels corresponding to the depicted food item.

For example, the method may comprise determining a first edge point and a second edge point in the first image, wherein the first edge point corresponds to a first edge of the food item or a container (e.g. plate) of the food item and the second edge point corresponds to a second edge of the food item or the container of the food item, and determining a number of pixels between the first edge point and the second edge point. In this example, estimating the quantity of the food item in block 208 may be based on a comparison between the determined number of pixels between the first and second edge points and the number of pixels corresponding to the detected first physical attribute of the first user. In some embodiments, more than one first images depicting the body part and the food item may be used to obtain multiple first and second edge points for the purpose of estimating the quantity of the food item. The accuracy of the quantity estimation may be improved by using multiple first images that are taken at different camera angles. It will be appreciated that other image processing techniques may also be used for extracting image pixels corresponding to the depicted food item, for example an image processing process which has been developed with a substantial data set and applying machine learning techniques (e.g. deep learning architecture).

In addition or alternatively, in some embodiments, the method may further comprise acquiring a camera angle at which the first image is taken. For example, the camera angle at which the image is taken may be obtained via accelerometer (or orientation sensor) in a smartphone or a tablet. In these embodiments, estimating the quantity of the depicted food item in block 208 may be further based on the acquired camera angle at which the first image is taken. Moreover, in some embodiments the method may comprise receiving a user input indicating a size and/or a shape of a container of the food item depicted in the first image (e.g. whether the container is in a rectangular shape), and the quantity estimation may be performed further based on the received user input indicating a size and/or shape of the container.

In some embodiments, the method may further comprise acquiring a supplementary image depicting the body part of the first user. The supplementary may be taken at a camera angle different from that of the first image. In these embodiments, the method may further comprise performing, based on the supplementary image, detection of the first physical attribute of the body part of the first user, and updating the value of the first physical attribute of the body part of the first user based on comparison between the result of the detection based on the first image and the result of the detection based on the supplementary image.

In some embodiments, subsequent to block 208, the method may further comprise determining a characteristic associated with the quantity of the food item depicted in the first image, based on the quantity of the food item estimated in block 208. The characteristic associated with the quantity of the food item may be one of: an amount of dietary energy in the food item, an amount of protein in the food item, an amount of carbohydrate in the food item, an amount of mineral in the food item, an amount of vitamins in the food item, an amount of dietary fiber in the food item, and an amount of sugar in the food item.

Figure 4A:
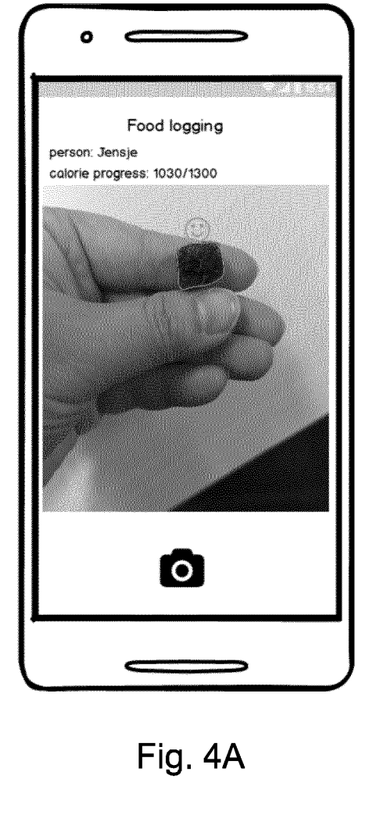
FIG. 4A and FIG. 4B are exemplary drawings of the method of FIG. 2 being implemented in a smartphone device.
Figure 4B:
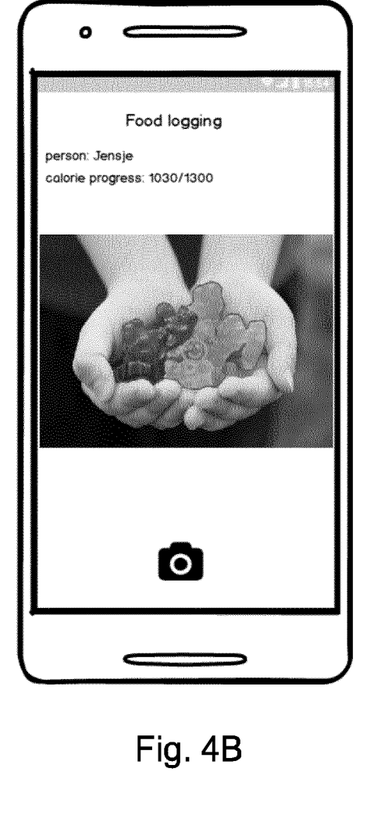

In some embodiments, the determined characteristic associated with the quantity of the food item may be used in tracking and monitoring a dietary progress of a user. To illustrate this aspect in further detail, exemplary drawings of the method described herein being implemented in a smartphone device are shown in FIG. 4A and FIG. 4B. More specifically, FIG. 4A and FIG. 4B show a virtual interface displayed at a smartphone device, the virtual interface providing information associated with a user (e.g. the name of the user "Jensje"), a dietary progress of the user (e.g. "calorie progress: 1030/1300"), as well as the acquired first image which depicts a body part of the user and a food item. The acquired first image in the example of FIG. 4A depicts a part of the user's hand, while the acquired first image in the example of FIG. 4B depicts both of the user's hands.

In both examples of FIG. 4A and FIG. 4B, the food item being held by the user in the acquired first image is identified and the quantity of the food item is estimated in accordance to the method as described above. Subsequently, an amount of dietary energy in the depicted food item is determined based on the estimated quantity of the food item, and the determined amount of dietary energy (in units of calories) is compared against the amount of remaining dietary energy allowed for the user (i.e. a predetermined daily dietary energy allowance minus an amount of consumed dietary energy today). In this example, the amount of remaining dietary energy allowed for the user "Jensje" is 270 kcal (based on the calculation 1300 kcal−1030 kcal=270 kcal). Hence, if the depicted food item has a determined dietary energy less than 270 kcal, an indication such as a smiley face overlaying the first image can be provided at the virtual interface (see FIG. 4A, for example). In contrast, if the depicted food item has a determined dietary energy more than 270 kcal, an indication such as a red outline surrounding the food item overlaying the first image can be provided at the virtual interface. In addition, a green outline surrounding only part of the quantity of the depicted food item overlaying the first image may also be provided to highlight a portion of the depicted food item that can be consumed by the user without exceeding the predetermined daily dietary energy allowance. It will be appreciated that other types of audio/visual/tactile indication may be provided to the user to signify whether the depicted food item falls within an "allowable" range in accordance to predetermined personal dietary intake requirement(s).

The method as described herein may be implemented as an application software on an electronic device, such as a smartphone or a tablet. The application software may be used by one or more users for the purpose of food logging (e.g. daily food log). Since the method as described herein allows a quantity of a food item to be estimated based on an image depicting the food item and a body part of a user, quantities of food items being consumed by user(s) can be estimated in a convenient and user-friendly manner. Due to the improved convenience, the method as described herein is especially advantageous for use cases including: on-the-go food consumption when containers (e.g. plates) and/or static reference objects are not available, social media sharing, and grocery shopping.

Figure 3:
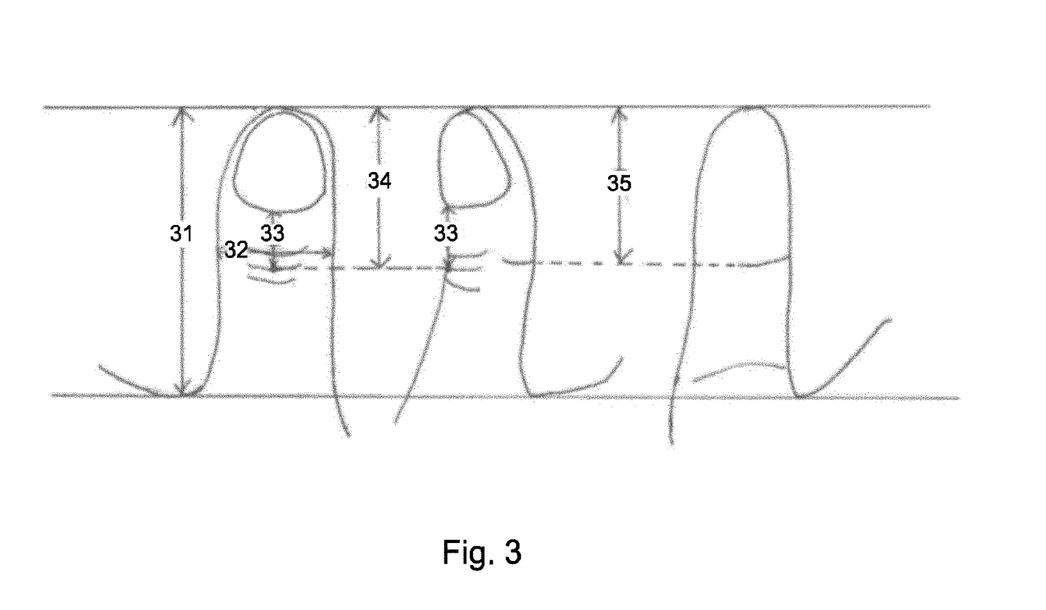
FIG. 3 illustrates a number of examples of physical attributes of a thumb of a user, according to an embodiment.

FIG. 3 illustrates a number of examples of physical attributes of a thumb of a user, according to an embodiment. In more detail, from left to right, a front face of the thumb, a side profile of the thumb, and a back face of the thumb are illustrated in FIG. 3.

The dimensions 31, 32, 33, 34, and 35 as indicated in FIG. 3 are respectively the length of the thumb (herein referred to as "thumb length"), the width of the thumb at the position of the distal knuckle (herein referred to as "thumb width"), the distance between the center point of the bottom of the fingernail and the center point of the middle wrinkle line on the front face of the thumb at the position of the distal knuckle, the distance between the tip of the thumb to the middle wrinkle line on the front face of the thumb at the position of the distal knuckle, and the distance between the tip of the thumb to the middle wrinkle line on the back face of the tube at the position of the distal knuckle.

As described above with reference to FIG. 2, in some embodiments the method may comprise acquiring, for each of a plurality of users, one or more physical attributes of the body part of the respective user. This process may be explained in more detail using the thumb of the respective user as an example. In some embodiments, the thumb length 31 and the thumb width 32 may be used in an initialization phase in which these two dimensions are acquired as physical attributes and subsequently associated with the respective user profiles in the user profile database.

Furthermore, during a calibration phase, a number of image-based detection techniques may be employed to acquire further physical attributes associated with the thumbnail and/or the thumb of the respective user. For example, image-based fingernail plate detection techniques may be used in this regard to determine, based on image(s) depicting the thumb of a respective user, the distance between the center point of the bottom of the fingernail and the center point of the middle wrinkle line on the front face of the thumb at the position of the distal knuckle. In more detail, one or more image descriptor features associated with the fingernail plate of the respective user can be determined, which can then be used for determining the distance between the center point of the bottom of the fingernail and the center point of the middle wrinkle line on the front face of the thumb at the position of the distal knuckle. In case a plurality of image descriptor features are determined from a plurality of images, at least one of the plurality of image descriptor features which has a high degree of certainty, reliability and/or robustness amongst the plurality of images may be selected as a first candidate image descriptor feature, the first candidate image descriptor feature being one that can be determined in subsequently acquired images including the thumb of the respective user. In addition or alternatively, at least one of the plurality of image descriptor features may be selected by a user as the first candidate image descriptor feature.

A second candidate image descriptor feature which correspond to more distinctive features of the hand of the user (e.g. the thenar, the side of a finger, and/or the pulp of a finger) may be also selected. The first candidate image descriptor feature and/or the second candidate image descriptor feature may further be used for calibrating previously acquired physical attributes (e.g. ones obtained during the initialization phase, including the distance between the center point of the bottom of the fingernail and the center point of the middle wrinkle line on the front face of the thumb at the position of the distal knuckle).

As another example, during the calibration phase, image-based edge detection techniques may be used to determine one or more of the physical attributes 31 to 35 as described above and shown in FIG. 3. Based on image(s) of the hand of the respective user, image pixels corresponding to edge features such as the side of a finger, the tip of a finger, a boundary of a fingernail, a wrinkle at the position of the distal knuckle of a finger, etc. in the image(s) can be detected. The image pixels corresponding to the edge features can then be used to determine at least one or more of the following physical attributes: thumb length, thumb width, the distance between the center point of the bottom of the fingernail and the center point of the middle wrinkle line on the front face of the thumb at the position of the distal knuckle, the distance between the tip of the thumb to the middle wrinkle line on the front face of the thumb at the position of the distal knuckle, and the distance between the tip of the thumb to the middle wrinkle line on the back face of the tube at the position of the distal knuckle. Furthermore, the physical attributes determined on the basis of edge detection techniques can be used for calibrating and/or confirming previously-acquired physical attributes.

There is thus provided an improved method and apparatus for performing image-based food quantity estimation, which overcomes the existing problems.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for performing image-based food quantity estimation, the method comprising:
    acquiring, via a user interface, for each of a plurality of users, one or more physical attributes of a body part of a respective user;
    associating, for each of the plurality of users, the acquired one or more physical attributes of the body part with a user profile of the respective user in a user profile database;
    acquiring, via the user interface, a first image, wherein the first image depicts a food item and a body part of a first user;
    detecting, via a processor, based on the acquired first image, a first physical attribute of the body part of the first user;
    identifying the first user by comparing the detected first physical attribute of the body part of the first user with corresponding type of physical attribute of the body part of the plurality of users stored in the user profile database;
    retrieving, via the processor, a second physical attribute of the body part of the first user from the user profile of the first user;
    identifying, based on the acquired first image, the depicted food item; and
    estimating, via the processor, a quantity of the food item depicted in the acquired first image based on the identified food item, the detected first physical attribute of the body part of the first user, and the retrieved second physical attribute of the body part of the first user.

2. The computer-implemented method according to claim 1, wherein acquiring one or more physical attributes of the body part of the respective user comprises:
    providing, at a touch screen display device, a virtual user interface including an interactive visual tool configured to allow a user to measure the one or more physical attributes of the body part of the respective user;
    receiving a user input via the virtual user interface, wherein the user input corresponds to a placement of at least a part of the body part at the touch screen display device; and
    determining the one or more physical attributes of the body part based on the received user input.

3. The computer-implemented method according to claim 2, wherein acquiring one or more physical attributes of the body part of the respective user comprises:
    acquiring a second image depicting the body part of the respective user;
    detecting, from the acquired second image, a first image descriptor feature associated with the body part of the respective user; and
    determining the one or more physical attributes based on the detected first image descriptor feature.

4. The computer-implemented method according to claim 3, further comprising:
    acquiring one or more manually-measured physical attributes of the body part of the respective user;
    comparing each of the one or more determined physical attributes respectively with corresponding one or more manually-measured physical attributes; and
    confirming or updating a value of the one or more physical attributes of the body part based on results of the comparison.

5. The computer-implemented method according to claim 4, further comprising performing the following steps for at least one of the plurality of users:
    acquiring one or more third images depicting the body part of the respective user;
    performing image processing of the acquired one or more third images depicting the body part of the respective user to obtain a second image descriptor feature associated with the body part of the respective user, wherein the image processing is performed based on a comparison between image pixels of the one or more third images;
    determining, based on the second image descriptor feature of the one or more third images, the one or more physical attributes of the body part of the respective user which correspond to the acquired one or more physical attributes of the body part of the respective user;
    calibrating the acquired one or more physical attributes of the body part of the respective user based on a comparison between the acquired one or more physical attributes and the one or more physical attributes determined based on the second image descriptor feature; and updating, based on results of the calibration, the one or more physical attributes of the body part associated with the user profile of the respective user.

6. The computer-implemented method according to claim 5, wherein the one or more of third images depicting the body part of the respective user are acquired, and a plurality of types of image descriptor features are obtained for each of the one or more of third images, and wherein acquiring one or more physical attributes of the body part of the respective user further comprises:

determining a degree of certainty of a type of image descriptor feature by comparing the types of image descriptor features of each of the one or more of third images; and selecting the type of image descriptor feature with a highest degree of certainty, wherein determining the one or more physical attributes of the body part of the respective user is based on one or more image descriptor features which correspond to the selected type of image descriptor feature with the highest degree of certainty.

7. The computer-implemented method according to claim 1, wherein acquiring the one or more physical attributes of the body part of the respective user comprises:

acquiring one or more physical characteristics of the respective user, wherein the one or more physical characteristics comprises at least one of: gender of the respective user, age of the respective user, height of the respective user, and weight of the respective user; and determining the one or more physical attributes of the body part of the respective user based on the one or more physical characteristics of the respective user.

8. The computer-implemented method according to claim 1, further comprising performing image processing on the first image to extract image pixels corresponding to the depicted food item, wherein estimating the quantity of the food item is based on a comparison between the extracted image pixels corresponding to the depicted food item.

9. The computer-implemented method according to claim 1, further comprising acquiring a camera angle at which the first image is taken, wherein estimating the quantity of the depicted food item is further based on the acquired camera angle.

10. The computer-implemented method according to claim 9, further comprising:

acquiring a supplementary image depicting the body part of the first user, wherein the supplementary image is taken at a different camera angle from that of the first image;

performing, based on the supplementary image, detection of the first physical attribute of the body part of the first user; and updating the value of the first physical attribute of the body part of the first user based on comparison between result of the detection based on the first image and result of the detection based on the supplementary image.

11. The computer-implemented method according to claim 9, further comprising determining a characteristic associated with the quantity of the food item depicted in the first image, based on the estimated quantity of the food item.

12. The computer-implemented method according to claim 11, wherein the characteristic associated with the quantity of the food item is one of: an amount of dietary energy in the food item, an amount of protein in the food item, an amount of carbohydrate in the food item, an amount of mineral in the food item, an amount of vitamins in the food item, an amount of dietary fiber in the food item, and an amount of sugar in the food item.

13. A computer program product comprising a non-transitory computer readable medium, the computer readable medium having computer readable code embodied therein, the computer readable code being configured such that, on execution by a suitable computer or processor, the computer or processor is caused to perform the method as claimed in claim 1.

14. An apparatus for performing image-based food quantity estimation, the apparatus comprising a processor configured to:

acquire, via a user interface, for each of a plurality of users, one or more physical attributes of a body part of a respective user;

associate, for each of the plurality of users, the acquired one or more physical attributes of the body part with a user profile of the respective user in a user profile database;

acquire, via the user interface, a first image, wherein the first image depicts a food item and a body part of a first user;

detect, based on the acquired first image, a first physical attribute of the body part of the first user;

identify the first user by comparing the detected first physical attribute of the body part of the first user with corresponding type of physical attribute of the body part of the plurality of users stored in the user profile database;

retrieve a second physical attribute of the body part of the first user from the user profile of the first user;

identify, based on the acquired first image, the depicted food item; and estimate a quantity of the food item depicted in the acquired first image based on the identified food item, the detected first physical attribute of the body part of the first user, and the retrieved second physical attribute of the body part of the first user.

* * * * *